(12) United States Patent  (10) Patent No.: US 8,459,256 B2
Roblejo  (45) Date of Patent: Jun. 11, 2013

(54) RESUSCITATION DEVICE

(76) Inventor: Conrad Roblejo, Marlton, NJ (US)

( * ) Notice: Subject to any disclaimer, the term of this patent is extended or adjusted under 35 U.S.C. 154(b) by 396 days.

(21) Appl. No.: 12/862,137

(22) Filed: Aug. 24, 2010

(65) Prior Publication Data

US 2012/0048267 A1 Mar. 1, 2012

(51) Int. Cl.
*A61M 16/00* (2006.01)
*A61M 29/00* (2006.01)

(52) U.S. Cl.
USPC .............. 128/203.11; 128/207.15; 606/192

(58) Field of Classification Search
USPC .......... 128/859–861, 200.15, 200.24, 202.28, 128/202.29, 203.11, 207.14–17; 604/96.01, 604/103.07; 606/191, 192, 196; 601/41–44
See application file for complete search history.

(56) References Cited

U.S. PATENT DOCUMENTS

| | | | |
|---|---|---|---|
| 3,057,347 A * | 10/1962 | Mcgee | 128/202.28 |
| 3,734,100 A * | 5/1973 | Walker et al. | 128/207.15 |
| 3,948,255 A * | 4/1976 | Davidson | 128/207.14 |
| 4,305,387 A | 12/1981 | Reist-Kundig | |
| 4,351,330 A * | 9/1982 | Scarberry | 128/207.15 |
| 4,535,765 A * | 8/1985 | Paoluccio et al. | 128/203.11 |
| 4,688,568 A * | 8/1987 | Frass et al. | 128/207.15 |
| 4,811,730 A | 3/1989 | Milano | |
| 4,834,085 A | 5/1989 | Webster | |
| 5,005,568 A | 4/1991 | Loescher | |
| 5,121,745 A | 6/1992 | Israel | |
| 5,584,288 A | 12/1996 | Baldwin | |

* cited by examiner

*Primary Examiner* — (Jackie) Tan-Uyen T. Ho
*Assistant Examiner* — Mark K Han
(74) *Attorney, Agent, or Firm* — Michael B. Fein; Eckert Seamans Cherin & Mellott

(57) ABSTRACT

A mouth-to-mouth resuscitation device comprising a straight blow-in tube having a proximal side and a distal side, a filter and one way valve on the proximal side for receiving exhaled breath from a mouth of a rescuer, an opening at the distal side for delivering the exhaled breath into the throat of a victim, an inflatable bladder surrounding the straight blow-in tube which, when inflated, assumes a donut shape which has a diameter of about 1.5" to 2.5", the bladder located on the straight blow-in tube between about 0.75" and 2.0" from the distal opening, an inflation tube in fluid communication with the inside of the inflatable bladder.

9 Claims, 2 Drawing Sheets

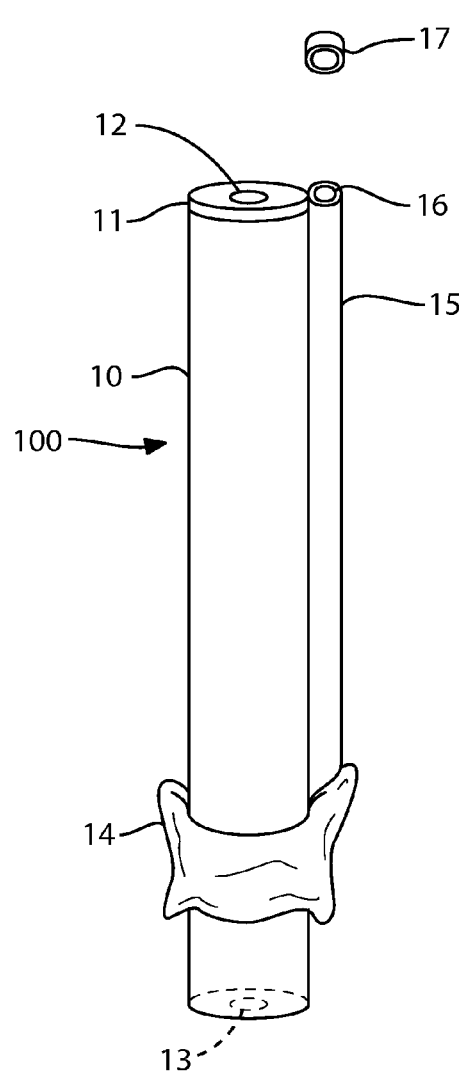 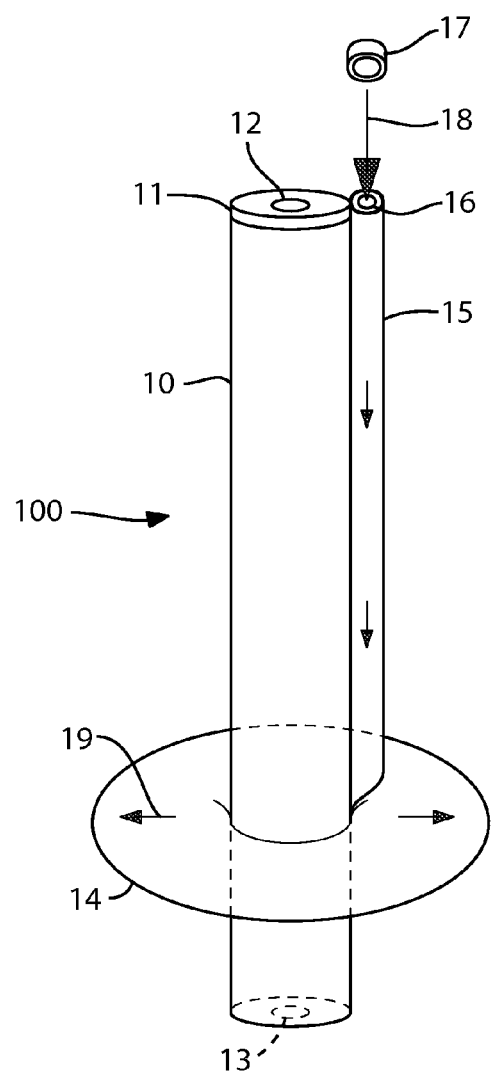
FIG. 1A
FIG. 1B

RESUSCITATION DEVICE

BACKGROUND OF THE INVENTION

The present invention relates to the field of mouth-to-mouth resuscitation devices.

Devices to facilitate mouth-to-mouth resuscitation and protect the rescuer and victim from exchange of biological fluids such as vomit and germs have been in use for many years. Many of such devices employ a one-way valve that is interposed between a mouth of a rescuer and a mouth of a victim who has stopped breathing and needs to be resuscitated to restore breathing.

Potential rescuers are sometimes hesitant to attempt resuscitation of a victim whose medical condition is unknown to the rescuer because of the possibility of infection with AIDS, tuberculosis, or other communicable diseases which can be spread through exchange of bodily fluids expelled through the victim's mouth.

Some of the existing devices are masks which cover the victim's mouth and nose, while others are much simpler but less effective. In many cases the mask devices are large and difficult to carry in a pocket or purse.

The level of technical sophistication in one-way valve structures for use in a resuscitation mask is shown in U.S. Pat. No. 4,811,730 ('730) issued Mar. 14, 1989 to A. J. J. Milano. The '730 patent teaches the use of a pair of one-way valves in a cardio pulmonary resuscitation (CPR) mask. One of the valves allows a rescuer's breath to pass into the nose and mouth of a victim while preventing the victim's exhaled breath from entering the rescuer's mouth. A second one-way valve member is provided to permit the rescuer's breath to pass therethrough and into an inflatable bladder while simultaneously preventing the air in the bladder from escaping. The inflatable bladder creates a resilient sealing means between a face of a victim and the resuscitation mask.

Israel, U.S. Pat. No. 5,121,745, discloses a self-inflatable rescue mask which is disposable and packaged in a carrying case which is shaped to receive the mask in flattened and folded shape and sealed with closure means. The inflated mask is shaped to enclose and seal the mouth and nose of the victim.

Reist-Kündig et al, U.S. Pat. No. 4,305,387, discloses a mouth closure for providing artificial respiration which comprises a deformable elliptical plate whose periphery is surrounded by a tube, wherein the mouth closure is placed in the dentilabial cavity of the victim's upper and lower jaws and thereby seals the cavity from the outside.

Baldwin, U.S. Pat. No. 5,584,288, discloses a resuscitation device having a pair of valves to prevent exhaled breath from reaching the mouth of the rescuer.

Webster, U.S. Pat. No. 4,834,085, discloses a resuscitation device with an inflatable cone-shaped mask at one end of a hollow housing and a mouthpiece attached to the other end, designed to prevent the exchange of bodily fluids between the rescuer and the victim.

Loescher, et al., U.S. Pat. No. 5,005,568, discloses an isolation valve which includes a housing having a fixed inlet pipe and a bacteria filter, preferably 3M "Filtrete" type G synthetic air filter.

Although there have been many different types of artificial respiration devices used or proposed in the prior art, none have been a simple, disposable, easily foldable and compact device which effectively seals the mouth of the victim to allow efficient transfer of breath from the rescuer to the victim while at the same time preventing the communication of fluids from or to the rescuer.

It is an object of the present invention to provide such a device and a corresponding method of using such a device.

SUMMARY OF THE INVENTION

These objects, and others which will become apparent from the following disclosure and accompanying drawings, are achieved by the present invention which comprises in one aspect a mouth-to-mouth resuscitation device comprising a straight blow-in tube having a proximal side and a distal side, a filter and one way valve on the proximal side for receiving exhaled breath from a mouth of a rescuer, an opening at the distal side for delivering the exhaled breath into the throat of a victim, an inflatable bladder surrounding the straight blow-in tube which, when inflated, assumes a donut shape which has a diameter of about 1.5" to 2.5", the bladder located on the straight blow-in tube between about 0.75" and 2.0" from the distal opening, an inflation tube in fluid communication with the inside of the inflatable bladder.

Some embodiments include a removable cap on the inflation tube whereas other embodiments include a one way valve in the inflation tube so that no air escapes from the bladder after it is inflated.

The filter and one way valve can be housed in a disk shaped member attached to the distal side which has an opening for receiving the exhaled breath from the rescuer.

While various dimensions are possible, preferably the straight blow-in tube is about 5 to 6 inches long and has a diameter of about 0.5 to 1.0 inches, and the inflation tube has a length of about 3 to 4 inches and a diameter of 0.2 to 0.5 inches.

The straight blow in tube and the inflation tube can be constructed of natural or synthetic rubber or any other inexpensive material so that the device can be folded to a compacted configuration, in some embodiments including a pocket size case so that the device can be carried in a pocket or purse and always be available.

The devices is easily used for artificial respiration by placing the distal side of the device in the mouth of a victim, inflating the bladder by blowing in the inflation tube so that the inflated bladder fills the mouth of the victim, blowing in the proximal side of the blow-in tube while simultaneously closing the victim's nose so that breath does not exit, refraining from blowing in the proximal side while releasing the victim's nose to allow breath to exit, and repeating the blowing in and releasing steps until the victim is resuscitated.

BRIEF DESCRIPTION OF THE DRAWINGS

The description set forth above, as well as other objects, features and advantages of the present invention, will be more fully appreciated by referring to the detailed description and the drawings that follow. The description is of the presently preferred but, nonetheless, illustrative embodiments in accordance with the present invention, when taken in conjunction with the accompanying drawing wherein:

FIG. 1A is a perspective elevational view of a device according to the invention with the bladder uninflated.

FIG. 1B is a perspective elevational view of the device of FIG. 1A with the bladder inflated.

DETAILED DESCRIPTION OF THE PREFERRED EMBODIMENTS OF THE INVENTION

Figure 2:
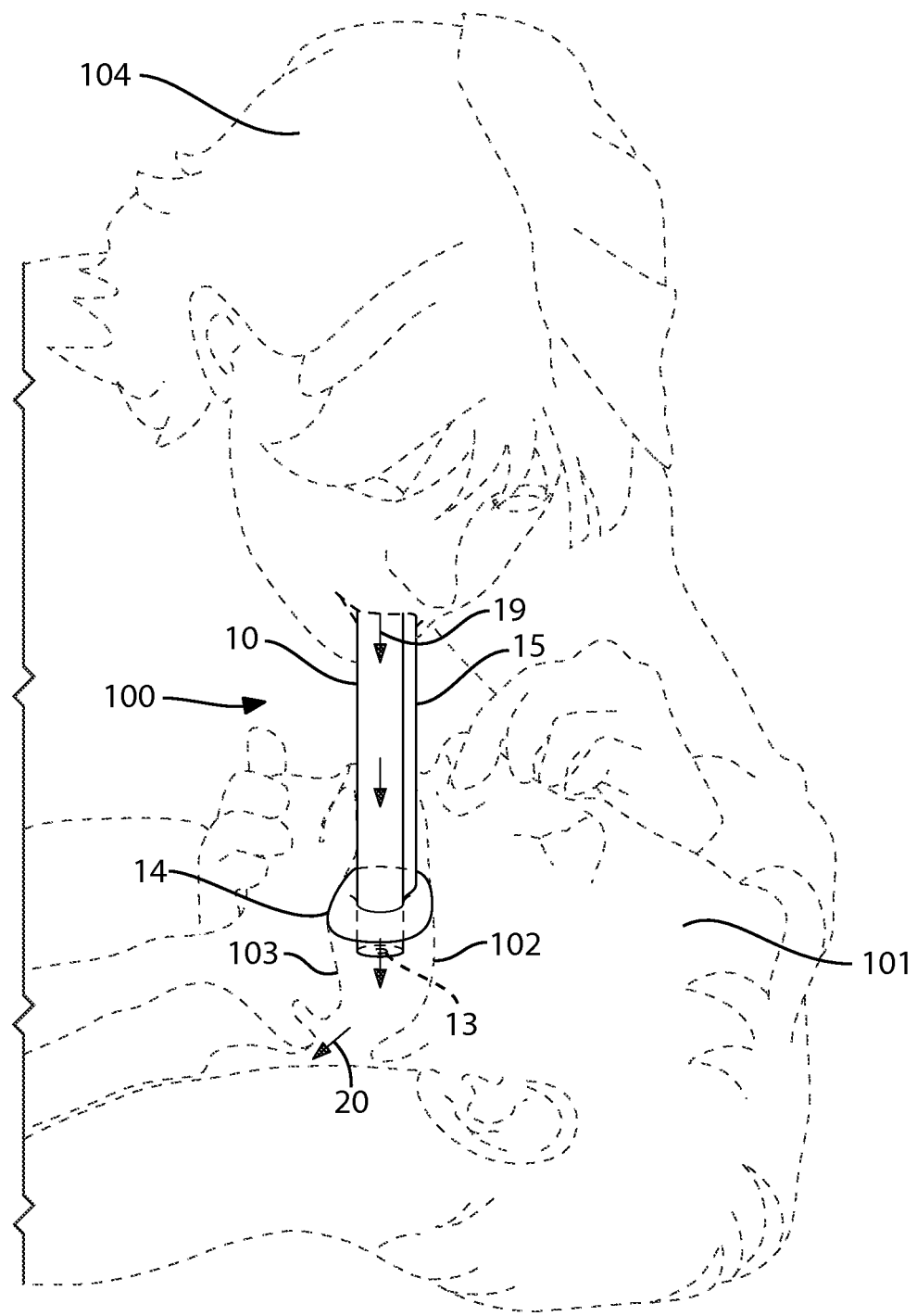
FIG. 2 is a perspective elevational view of the device of FIG. 1A with the bladder inflated, showing its placement in the mouth of a victim and its operation by a rescuer.

Reference is now made generally to FIG. 1A wherein a device 100 according to the invention is shown. A blow-in tube 10 has a disk-shaped member 11 which houses a filter and one-way valve at the proximal end whch has an air hole 12 for receiving breath of the rescuer. At the distal end there is an exit hole 13 through which the rescuer's breath exits and enters the throat of the victim.

Bladder 14 is disposed around blow-in tube 10 and is in fluid communication with inflation tube 15 which has a proximal opening 16 through which rescuer inflates the bladder 14, show as inflated in FIG. 1B. FIG. 1B shows the direction 18 of the breath of the rescuer into the inflation tube 15 which causes the bladder 14 to inflate outwardly in the direction of arrows 19. The illustrated embodiment includes a removable cap 17 on the inflation tube whereas other embodiments include a one way valve in the inflation tube so that no air escapes from the bladder after it is inflated.

FIG. 2 illustrates a rescuer 104 blowing into the proximal end of blow-in tube 10 in the direction of arrows 19 after bladder has already been inflated as show in FIG. 1A. The bladder is located between the palate 102 and tongue 103 of victim 101. The rescuer 104 is holding the nose of the victim 101 closed during the rescuer's exhale step, and will release the nose to allow breath to be exhaled from the victim 101 during the next step.

The device 100 of the invention has several advantages over prior art mouth-to-mouth resuscitation devices including, for example, the capability of quickly and effectively sealing off the victim's breath from exiting during the blow-in step and preventing vomit and other fluids from exiting the mouth of the victim during use. The device also has a filter and one way valve feature which prevent air from exiting the victim while the rescuer is supplying breath, and also preventing communication of diseases such as AIDS, tuberculosis, and the like.

Though the invention has been described with respect to a number of embodiments, many additional variations and modifications will immediately become apparent to those skilled in the art. It is therefore the intention that the appended claims be interpreted as broadly as possible in view of the prior art to include all such variations and modifications.

What is claimed is:

1. A mouth-to-mouth resuscitation device comprising a straight blow-in tube having a proximal side and a distal side, a filter and one way valve on the proximal side for receiving exhaled breath from a mouth of a rescuer, an opening at the distal side for delivering the exhaled breath into the throat of a victim, an inflatable bladder surrounding the straight blow-in tube which, when inflated, assumes a donut shape which has a diameter of about 1.5" to 2.5", the bladder located on the straight blow-in tube between about 0.75" and 2.0" from the distal opening, an inflation tube in fluid communication with the inside of the inflatable bladder.

2. The device of claim 1 further including a removable cap on the inflation tube.

3. The device of claim 1 further including a one way valve in the inflation tube so that no air escapes from the bladder after it is inflated.

4. The device of claim 1 wherein the filter and one way valve are housed in a disk shaped member attached to the distal side, the disk shaped member having an opening for receiving the exhaled breath from the rescuer.

5. The device of claim 1 wherein the straight blow-in tube is about 5 to 6 inches long and has a diameter of about 0.5 to 10 inches.

6. The device of claim 1 wherein the inflation tube has a length of about 3 to 4 inches and a diameter of 0.2 to 0.5 inches.

7. The device of claim 1 wherein the straight blow in tube and the inflation tube are constructed of natural or synthetic rubber and are foldable to a compacted configuration.

8. The device of claim 1 wherein the straight blow in tube and the inflation tube are constructed of natural or synthetic rubber and are foldable to a compacted configuration, further including a pocket size case.

9. A method of artificial respiration comprising placing the distal side of a device according to claim 1 in the mouth of a victim, inflating the bladder by blowing in the inflation tube so that the inflated bladder fills the mouth of the victim, blowing in the proximal side of the blow-in tube while simultaneously closing the victim's nose so that breath does not exit, refraining from blowing in the proximal side while releasing the victim's nose to allow breath to exit, and repeating the blowing in and releasing steps until the victim is resuscitated.

* * * * *